US012576233B2

(12) United States Patent
Boulanger et al.

(10) Patent No.: US 12,576,233 B2
(45) Date of Patent: ***Mar. 17, 2026

(54) NO DELIVERY DEVICE WITH EMERGENCY DOSING SYSTEM

(71) Applicant: INOSYSTEMS, Antony (FR)

(72) Inventors: Thierry Boulanger, Antony (FR); Frédéric Marchal, Antony (FR); Mary Schmitt, Bagneux (FR)

(73) Assignee: INOSYSTEMS, Antony (FR)

( * ) Notice: Subject to any disclaimer, the term of this patent is extended or adjusted under 35 U.S.C. 154(b) by 616 days.

This patent is subject to a terminal disclaimer.

(21) Appl. No.: 18/093,094

(22) Filed: Jan. 4, 2023

(65) Prior Publication Data

US 2023/0211113 A1      Jul. 6, 2023

(30) Foreign Application Priority Data

Jan. 5, 2022   (FR) ........................................ 2200064
Jul. 18, 2022   (FR) ........................................ 2207324

(51) Int. Cl.
A61M 16/12        (2006.01)
A61M 16/00        (2006.01)
(Continued)

(52) U.S. Cl.
CPC .......... A61M 16/12 (2013.01); A61M 16/024 (2017.08); A61M 16/202 (2014.02);
(Continued)

(58) Field of Classification Search
CPC ............ A61M 16/0051; A61M 16/024; A61M 16/10; A61M 16/12; A61M 16/122;
(Continued)

(56) References Cited

U.S. PATENT DOCUMENTS

2025/0213812 A1*   7/2025   Boulanger ............ A61M 16/12

FOREIGN PATENT DOCUMENTS

EP          2 522 384        11/2012
EP          2522384 A1 *   11/2012 ............. A61B 5/082
(Continued)

OTHER PUBLICATIONS

English translation of EP-2522384-A1.*
Search Report and Written Opinion for FR2200064, dated Sep. 28, 2022, 8 pages.

*Primary Examiner* — Joseph D. Boecker
(74) *Attorney, Agent, or Firm* — Quantum Patent Law Firm; Seongyoune Kang

(57)        ABSTRACT

Disclosed is an NO delivery device for supplying an NO-containing gas, including an NO injection line, a flow rate measurement device and a valve device. The valve device is normally closed. An emergency line connected to the injection line includes an emergency solenoid valve, which is normally open, and a flow rate control device. An operating unit operates these elements. In the event of malfunction of the operating unit, the emergency solenoid valve passes to an open position, whilst the valve device passes to a closed position. The flow rate control device supplies the gas at a pre-fixed emergency flow rate of gas, determined on the basis of the gas flow rate measurements supplied by the flow rate measurement device during the normal functioning of the device prior to the malfunction. Gas supply installation including such an NO delivery device and a medical ventilator.

19 Claims, 3 Drawing Sheets

(51) Int. Cl.
    *A61M 16/16*       (2006.01)
    *A61M 16/20*       (2006.01)

(52) U.S. Cl.
    CPC ... *A61M 16/203* (2014.02); *A61M 2016/0027* (2013.01); *A61M 2016/0039* (2013.01); *A61M 16/0051* (2013.01); *A61M 16/16* (2013.01); *A61M 2202/0275* (2013.01); *A61M 2205/16* (2013.01); *A61M 2205/3334* (2013.01)

(58) Field of Classification Search
    CPC .............. A61M 16/125; A61M 16/202; A61M 16/203; A61M 16/204; A61M 2202/0275; A61M 2205/16; A61M 2205/3334; A61M 2016/0027; A61M 2016/0039; A61M 2016/102
    See application file for complete search history.

(56)               References Cited

FOREIGN PATENT DOCUMENTS

| | | | |
|---|---|---|---|
| EP | 3 888 727 | 10/2021 | |
| FR | 3079752 A1 * | 10/2019 | .......... A61M 16/208 |

* cited by examiner

210

NO DELIVERY DEVICE WITH EMERGENCY DOSING SYSTEM

This application claims priority to FR Patent Application No. 2207324 filed Jul. 18, 2022, and FR Patent Application No. 2200064 filed Jan. 5, 2022, the entire contents of each of which are hereby incorporated by reference.

BACKGROUND OF THE INVENTION

Field of the Invention

The invention relates to a device for delivering gaseous nitric oxide (NO) to a patient, comprising an NO emergency dosing system and intended to be connected to the patient circuit of a mechanical ventilator, that is to say a medical apparatus for administering gas to a patient, which makes it possible to supply the gas at a pre-fixed flow rate in the event of malfunction, in particular of the operating means.

Description of the Related Art

NO is a gas which, when inhaled, dilates the pulmonary vessels and increases oxygenation by improving gas exchange.

The properties of NO are used to treat various medical conditions such as persistent pulmonary hypertension of the newborn (PPHN), acute respiratory distress syndrome (ARDS) observed mainly in adults, or pulmonary hypertension in cardiac surgery, as disclosed in particular by EP-A-560928, EP-A-1516639 or U.S. Pat. No. 10,201,564.

Usually, a small quantity of gaseous NO (i.e. a few ppm by volume), diluted in nitrogen ($N_2$), is injected into a gaseous flow containing oxygen ($O_2$), which is then inhaled by the patient. The concentration of NO, which corresponds to a dosage, is determined by the physician or similar. Typically, the gas containing oxygen is usually a mixture of $N_2/O_2$ or air, such as medical-grade air. Generally, the concentration of NO in the gas inhaled by the patient is between 1 and 80 ppm by volume (ppmv), depending on the population treated, i.e. neonates or adults, and therefore the disease to be treated.

The gas inhaled by the patient can be delivered by way of an NO delivery device combined with a mechanical ventilator, as is described by U.S. Pat. No. 5,558,083. The NO delivery device is fluidically connected to one or more gas cylinders containing an $N_2/NO$ mixture, of which the concentration of NO can be between typically 200 and 800 ppmv. Generally, the NO delivery system comprises an NO injection module placed in the inhalation branch of a patient circuit connected fluidically, on the one hand, to the mechanical ventilator and, on the other hand, to a respiratory interface delivering the NO-enriched gas to the patient, for example a breathing mask, a tracheal intubation tube or similar.

The NO delivery system also comprises a flow rate sensor which measures the gaseous flow rate delivered by the mechanical ventilator (i.e. air or $N_2/O_2$ mixture) in order to determine the quantity of NO to be delivered in order to satisfy the dosage set by the physician.

The NO delivery system can ensure the NO dosage by way of a proportional solenoid valve which delivers a continuous flow of NO-containing gas and which is associated with a flow rate sensor, the two components being arranged in the delivery system, and an injection line connected to the NO injection module, as described in U.S. Pat. No. 5,558,083.

Other systems are available in which the proportional solenoid valve is replaced by a plurality of "all-or-nothing" solenoid valves, delivering the gas intermittently, that is to say in the form of pulses, generally at a high frequency, of which the amplitude and the duration guarantee a good quality of gas circulating in the injection line connected to the NO injection module.

In all cases, the known NO delivery systems receive the measurements of the flow rate sensor placed in the inhalation branch of the patient circuit and adjust in real time the quantity of NO to be delivered, according to the desired dosage, by controlling the flow of NO in the injection line.

Since NO is a therapeutically effective agent, that is to say very small concentrations (i.e. a few ppmv) produce a therapeutic effect, its correct dosing is of critical importance, and medical personnel have to constantly adjust the dosage according to the condition of the patient.

When the patient's condition changes, the concentration of NO has to be gradually reduced or increased. For example, in a situation of withdrawal from a neonate whose condition is improving, it is customary to gradually reduce the dosage, for example in steps of 1 ppm, until a zero value is reached, making it possible then to stop the NO delivery system.

Gradual reduction of the NO concentration makes it possible to avoid a "rebound effect", which may occur in cases of rapid variation of the concentration, for example in cases of abrupt discontinuation of the treatment, the effect being to seriously worsen the condition of the patient.

However, NO delivery systems are sophisticated electrical medical systems which are susceptible to faults or malfunctions that may have a considerable impact on the therapy that is being provided. For example, a major electrical fault or malfunction, in particular of the operating means, may cause a breakdown of the apparatus and therefore a total shut-down of NO delivery, with the negative consequences mentioned above.

Under such circumstances, the device has to alert the user, by means of an audible alarm signal, that prompt action is required, for example to switch to an emergency pneumatic injection mode so as to limit as far as possible the undesirable effects associated with discontinuation of the therapy.

This switching to an emergency mode is usually done by actuating a rotary knob that commands the change-over from the normal NO administration mode to an emergency mode in which there is, for example, a continuous delivery of a fixed flow rate of $N_2/NO$, i.e. of the order of 250 ml/min.

However, an emergency dosing mechanism or system is not without risk, in particular for the following reasons:

its activation requires the presence of a person who is authorized to take this action, for example a specialist in neonatology. Several minutes may therefore go by before this person arrives and thus before the emergency dose is established, and this entails a discontinuation of the therapy and exposes the patient to a rebound effect.

this emergency dose, i.e. a unique flow rate of $N_2/NO$ mixture, cannot guarantee that the desired dosage is satisfied. In particular, when the emergency dose is much below the desired dosage, the patient may be exposed to an abrupt change of concentration and may potentially be subject to considerable adverse effects.

the emergency dose is incompatible with some types of ventilators delivering very small volumes, such as high-frequency oscillation (HFO) ventilators, since it may result in an inhaled NO concentration that is too high and that may reach levels that are dangerous to the patient. Therefore, when the patient is being treated with such a ventilator (i.e. HFO ventilator), one finds oneself without means of administering NO to the patient, and this entails the abovementioned risks associated with the abrupt stoppage of treatment.

It therefore appears that the current emergency dosing mechanisms cannot guarantee a satisfactory level of safety and that it would be desirable for the patient, in the case of an emergency dose being applied due to malfunction of the NO delivery system, to be able to maintain NO therapy without interrupting the therapy and without worrying about the type of ventilator, i.e. HFO ventilator or others, with which the NO delivery system cooperates.

In other words, a problem is to be able to maintain a dosage, that is to say a treatment of the patient by inhaled NO, even in cases of a fault or malfunction of the NO delivery system, in particular a total functional shut-down of the operating means on account of a breakdown or a fault in the electrical power supply, for example.

SUMMARY OF THE INVENTION

A solution according to the invention concerns an NO delivery device, i.e. an apparatus, for supplying an NO-containing gas, typically an NO/nitrogen mixture, comprising an NO injection line for conveying the NO-containing gas, a valve device arranged on the injection line in order to control the circulation of the NO-containing gas in the injection line, said valve device being configured to be normally in a closed position for preventing any circulation of gas in the injection line, a flow rate measurement device arranged on the injection line in order to perform one or more measurements of the flow rate of the NO-containing gas circulating in the injection line, an emergency line which connects fluidically to the injection line upstream and downstream of the valve device, said emergency line comprising an emergency solenoid valve configured to be normally in an open position in order to permit a circulation of gas in the emergency line, and a flow rate control device, and operating means, also called an operating unit, configured to cooperate with the emergency solenoid valve, the flow rate control device, the valve device and the flow rate measurement device.

Moreover, in the device according to the invention, in the event of malfunction (i.e. within the NO delivery device) generating a shut-down of all cooperation with the operating means:

the emergency solenoid valve is configured to pass to an open position in order to permit a circulation of gas in the emergency line, the valve device is configured to pass to a closed position in order to stop all circulation of gas in the injection line, and the flow rate control device is configured to supply the gas at a pre-fixed emergency flow rate of gas, where said emergency flow rate of gas:

is determined by the operating means on the basis of at least one gas flow rate measurement supplied by the flow rate measurement device, during a normal functioning of the device prior to said malfunction, and is pre-regulated through command of said flow rate control device by the operating means, during said normal functioning of the device.

In the context of the invention:

"ppmv" signifies parts per million by volume,

% vol. signifies percentage by volume,

NO designates nitric oxide, $N_2$ designates nitrogen, $O_2$ designates oxygen.

"Normal functioning" is understood to mean the customary functioning of the NO delivery device during a first period of time (of non-zero duration), in the absence of any breakdown, malfunction, fault or the like. The first period of time has a duration of typically one to several minutes, even hours or more.

"Malfunction" is understood to mean a breakdown, an anomaly, a problem, a fault or similar, whether electrical, mechanical or of another kind, affecting the normal functioning of the NO delivery device, in particular preventing the functioning of the means of operating the device, during a second period of time (of non-zero duration), for example on account of a breakdown of the operating means, typically a fault in the electrical power supply to the latter. The second period of time has a variable duration, for example from a few seconds to one or more minutes, or tens of minutes, or even more.

According to the embodiment considered, the NO delivery device of the invention can comprise one or more of the following features:

the operating means are further configured in order, during the normal functioning of the device, to command the emergency solenoid valve such that the latter is in a closed position preventing any circulation of gas in the emergency line.

the operating means are further configured in order, during the normal functioning of the device, to command the valve device to enable a circulation of gas in the injection line and to permit at least one measurement of gas flow rate by the flow rate measurement device.

the operating means are further configured in order, during the normal functioning of the device, to control the flow rate control device in order to pre-regulate the emergency gas flow rate on the basis of at least one gas flow rate measurement supplied by the flow rate measurement device. In other words, the flow rate control device is adjusted before any malfunction, that is to say while the device is functioning normally.

during the normal functioning of the device, the flow rate measurement device is configured to perform several successive flow rate measurements.

during the normal functioning of the device, the operating means are further configured to determine, for example calculate, the emergency gas flow rate on the basis of one or more flow rate measurements performed by the flow rate measurement device.

the emergency line connects fluidically to the injection line upstream of the valve device, and upstream or downstream of the flow rate measurement device, preferably downstream of the flow rate measurement device.

a flow rate measurement device is arranged on the injection line, downstream or upstream of the valve device, preferably downstream of the valve device, the emergency line connects fluidically to the injection line via an upstream end, upstream of the valve device, and via a downstream end, downstream of the valve device, so as to bypass said valve device.

it comprises storage means for storing at least some of the successive flow rate measurements performed by the flow rate measurement device, that is to say the successive flow rate measurements are stored by storage means.

the storage means comprise a computer memory, for example a random access memory or other memory.

it comprises an NO emergency dosing system comprising the emergency line.

the NO-conveying line conveys a gaseous mixture formed of NO and nitrogen, preferably a gaseous mixture $NO/N_2$ (i.e. nitric oxide/nitrogen) containing between 100 and 2000 ppmv of NO, typically less than 1000 ppmv of NO, the remainder being nitrogen (and, possibly, unavoidable impurities).

the emergency solenoid valve is configured and/or operated to be normally open.

the emergency solenoid valve is of the all-or-nothing type.

the operating means comprise at least one microprocessor.

the operating means comprise an electronic board carrying said at least one microprocessor.

the injection line is connected fluidically to a high-pressure line by way of a pressure-regulating device, the high-pressure line and the pressure-regulating device being arranged in the NO delivery device.

the NO delivery device comprises a casing.

the NO emergency dosing system is arranged in the casing, in particular the emergency line and the emergency solenoid valve.

the emergency line connects fluidically to the injection line between the pressure-regulating device and the valve device.

the valve device comprises a solenoid valve, preferably a proportional solenoid valve.

the flow rate control device is configured to form, constitute or comprise a calibrated orifice of the proportional type, that is to say to form a system with a proportional calibrated orifice.

the flow rate control device comprises an actuator means cooperating with a movable element.

the flow rate control device comprises an actuator means cooperating with a movable element comprising a continuous recess.

the movable element is configured to be displaced angularly by the actuator means of the flow rate control device.

the actuator means comprises an electric motor powered by the electrical power supply means, i.e. during the normal functioning.

the actuator means comprises an electric motor driving a rotary shaft, the movable element being rigidly connected to said rotary shaft.

the electric motor is a stepping motor.

the movable element is arranged movably in an inner housing comprising an inlet port and an outlet port in fluidic communication with the emergency line.

the movable element is a sphere, that is to say spherical, for example a ball or the like.

the inner housing has a spherical shape matching that of the spherical movable element.

the operating means are configured for operating the actuator means in order to perform an angular displacement of the movable element between at least:

a position of total opening, corresponding to a level of total opening of the calibrated orifice of the flow rate control device, a position of total closure, corresponding to a level of total closure (i.e. occlusion) of the calibrated orifice of the flow rate control device, and at least one intermediate position situated between said position of total opening and said position of total closure, corresponding to a level of partial opening of the calibrated orifice of the flow rate control device.

the operating means are configured for operating the actuator means in order to perform a displacement, preferably an angular displacement, of the movable element between at least:

a position of total opening in which the entire gaseous flow conveyed via the emergency line penetrates the continuous recess of the movable element, that is to say a maximum flow rate, a position of total closure in which no gaseous flow can pass through the continuous recess of the movable element, that is to say a zero flow rate, and at least one intermediate position situated between said position of total opening and said position of total closure, in which only some of the gaseous flow conveyed via the emergency line penetrates the continuous recess of the movable element, that is to say one or more reduced flow rates.

the operating means are configured for operating the actuator means in order to perform an displacement, preferably an angular displacement, of the movable element between several intermediate positions angularly offset from each other, each corresponding to a level of opening of the calibrated orifice and/or to a given flow rate of gas, that is to say reduced flow rates between the maximum flow rate and the zero flow rate.

the operating means are configured for operating the actuator means during the normal functioning of the device, that is to say before any malfunction, in such a way as to regulate or adjust the pre-fixed emergency flow rate of gas.

the operating means are configured for operating the actuator means in order to perform a displacement, preferably an angular displacement, of the movable element in a given position corresponding to the pre-regulated emergency flow rate.

the operating means are configured to determine the opening of given calibrated orifice and/or the pre-regulated emergency flow rate on the basis of a stored lookup table.

the operating means are configured to determine an opening of given calibrated orifice corresponding to the pre-regulated emergency flow rate.

the lookup table is stored by the storage means, such as a computer memory.

it comprises electrical power supply means which are configured to supply electric current to the components that require electrical energy in order to function, in particular the operating means or other components, such as the solenoid valves, the electric motor, etc.

the electrical power supply means comprise means for connection to the mains (110/220V) and/or a battery or similar.

the flow rate control device of the NO emergency dosing system constitutes a system with a proportional calibrated orifice making it possible to regulate or adjust the pre-fixed emergency flow rate of gas, prior to any malfunction of the apparatus preventing cooperation between the operating means and the emergency solenoid valve, the flow rate control device, the valve device and/or the flow rate measurement device.

the emergency flow rate of gas corresponds to the last flow rate measurement performed by the flow rate measurement device that was performed prior to the malfunction.

According to a particular embodiment, the invention also relates to an NO delivery device for supplying an NO-containing gas, comprising:

an NO injection line for conveying the NO-containing gas, a valve device arranged on the injection line in order to control the circulation of the NO-containing gas in the injection line, a flow rate measurement device arranged on the injection line, downstream of the valve device, an NO emergency dosing system, operating means, and electrical power supply means supplying electric current to at least the operating means, in which the NO emergency dosing system comprises an emergency line fluidically connecting to the injection line upstream of the valve device, said emergency line comprising an emergency solenoid valve and a flow rate control device forming a system with a proportional calibrated orifice, the emergency solenoid valve and the control device being operated by the operating means, and in which:

the operating means are configured to:

a) calculate a mean NO flow rate from the NO flow rate that has circulated in the injection line for a given time, that is to say during the normal functioning of the NO delivery device, and b) control the flow rate control device in order to pre-regulate a given level of opening of the calibrated orifice of the flow rate control device, that is to say during the normal functioning of the NO delivery device, c) and, in the event of a malfunction, that is to say a major failure of the NO delivery device or an interruption in the electrical power supply to the NO delivery device, i) the valve device is configured to pass to a closed position in order to prevent the passage of the gas, i.e. of the mixture $NO/N_2$, in the injection line, and ii) the emergency solenoid valve is configured to pass to an open position in order to enable the passage of the gas, i.e. of the mixture $NO/N_2$, in the emergency line at a flow rate fixed by the level of opening of the calibrated orifice corresponding to the last value of mean NO flow rate determined by the operating unit, that is to say the last valid value of mean NO flow rate that was determined before a malfunction, that is to say during the normal functioning prior to this malfunction.

The invention also relates to an installation for supplying gas to a patient, that is to say a human being, comprising:

at least one source of NO containing a gaseous mixture $NO/N_2$, an NO delivery device according to the invention, supplied with a gaseous mixture $NO/N_2$ by said at least one NO source, an inhalation branch of a patient circuit supplied with a gaseous mixture $NO/N_2$ by the NO delivery device, and a medical ventilator, i.e. a respiratory assistance apparatus, in fluidic communication with the inhalation branch in order to supply said inhalation branch with a respiratory gas containing at least 21% of oxygen.

According to the embodiment considered, the gas supply installation of the invention may comprise one or more of the following features:

the medical ventilator delivers air or an oxygen/nitrogen mixture, i.e. as respiratory gas containing at least 21% by volume of oxygen.

according to one embodiment, the medical ventilator comprises a motorized blower (i.e. turbine, compressor or similar) delivering the respiratory gas, typically air or an oxygen/nitrogen mixture.

according to another embodiment, the medical ventilator comprises an internal gas circuit comprising one or more proportional valves for conveying the gas and controlling its delivery, in particular its flow rate. Such a ventilator is generally supplied with respiratory gas via one or more wall outlets supplied with gas from a network of channels in a hospital building, typically with air or an oxygen/nitrogen mixture.

the medical ventilator comprises control means, such as one or more electronic control boards.

the control means, such as an electronic control board, operate or control the motorized blower or, depending on the circumstances, the proportional valves of the medical ventilator.

the medical ventilator is of the HFO type or comprises an HFO function, that is to say it is able to produce high-frequency oscillations.

the NO source contains a gaseous mixture $NO/N_2$ containing between 100 and 2000 ppmv of NO, the remainder being nitrogen ($N_2$), stored at a pressure of between 10 and 250 bar abs, typically at over 100 bar abs (before start of withdrawal).

the NO source contains a gaseous mixture $NO/N_2$ containing between 100 and 1000 ppmv of NO, the remainder being nitrogen ($N_2$), stored at a pressure of between 10 and 250 bar abs, typically at over 100 bar abs (before start of withdrawal).

the NO source is in the form of one or more pressurized gas cylinders.

the NO source is in the form of one or more gas cylinders having a capacity of between 0.5 and 50 l (water equivalent).

the gas cylinder comprises a cylindrical body made of steel or of aluminium alloy.

the gas cylinder is equipped with a simple valve (without regulator) or one with an integrated regulator.

the gas cylinder is provided with a regulator valve protected by a protective cap, for example made of metal or polymer.

the patient circuit comprises an inhalation branch and an exhalation branch.

the patient circuit comprises flexible ducts forming the inhalation branch and the exhalation branch, typically hoses made of polymer.

the inhalation branch and the exhalation branch, e.g. flexible ducts, are connected to a joining piece, such as a Y-piece.

the inhalation branch and/or the exhalation branch are connected fluidically to a patient respiratory interface, preferably via the joining piece.

the patient respiratory interface comprises a tracheal intubation probe or a breathing mask.

the inhalation branch and the exhalation branch comprise flexible ducts, for example made of polymer.

the inhalation branch and the exhalation branch are moreover fluidically connected to outlet and inlet orifices, respectively, of the medical ventilator.

the inhalation branch of the patient circuit can comprise a gas humidifier.

the gas humidifier is arranged downstream of the NO injection module in such a way as to be able to humidify the gas before the latter is administered by inhalation to the patient.

According to another aspect, the invention also relates to a method for therapeutic treatment of a person, i.e. a patient (adult, child, adolescent or neonate), suffering from pulmonary hypertension and/or hypoxia, which cause pulmonary vasoconstriction or similar, said method comprising administration by inhalation, to the person (i.e. human being) requiring it, of a gaseous mixture containing from 1 to 80 ppmv of NO and at least 21% by volume of oxygen by means of a gas delivery installation, as described above, comprising an NO delivery device equipped with the NO emergency dosing system according to the invention, so as to treat (at least partially) said pulmonary hypertension and/or said hypoxia, which can be caused by one or more pulmonary diseases or disorders such as PPHN (persistent pulmonary hypertension of the newborn) or ARDS (acute respiratory distress syndrome) or can be caused by heart surgery with placement of the patient on extracorporeal blood circulation.

BRIEF DESCRIPTION OF THE DRAWINGS

The invention will now be better understood from the following detailed description, which is given by way of non-limiting illustration, with reference to the appended figures, in which.

DESCRIPTION OF THE PREFERRED EMBODIMENTS

Figure 1:
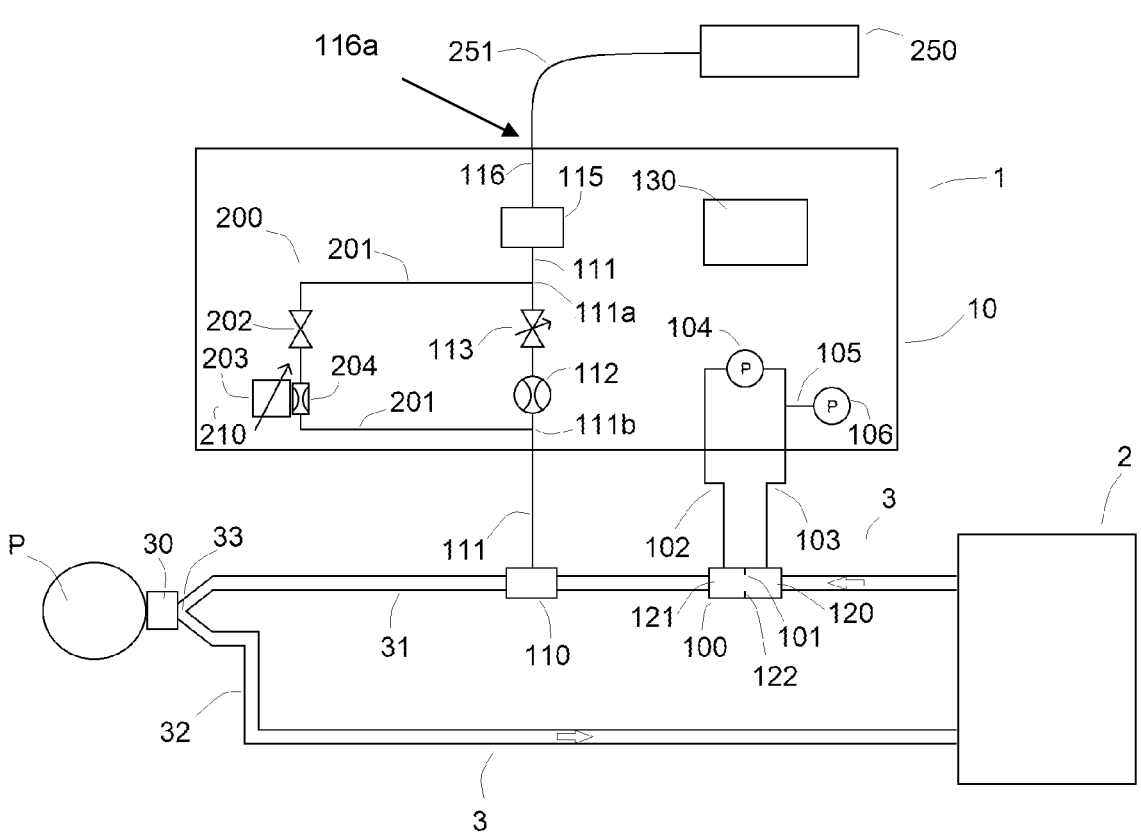
FIG. 1 is a schematic representation of an embodiment of a gas delivery installation comprising an NO delivery device equipped with an NO emergency dosing system according to the present invention.

FIG. 1 is a schematic representation of an embodiment of a gas delivery installation 1, 2 according to the present invention, comprising an NO delivery device 1, comprising an NO emergency dosing mechanism, associated with a mechanical ventilator 2, that is to say a respiratory apparatus delivering a respiratory gas, which installation is configured to deliver NO in gaseous form to a patient at a desired concentration corresponding to a dosage set by an anaesthetist or the like, typically between 1 and 80 ppmv of NO (i.e. ppm by volume).

The medical ventilator 2 delivers a respiratory gas containing at least 21% of oxygen, such as air or an NO/$N_2$ mixture, into a patient circuit 3, in particular into an inhalation branch 31 of said patient circuit 3, serving to convey and supply the respiratory gas to a patient P during the inhalation phases of the latter, that is to say to supply respiratory assistance to the patient P, and to transport the gases exhaled by the patient during the exhalation phases of the latter.

The medical ventilator 2 is a conventional respiratory assistance apparatus which, depending on the desired embodiment, can comprise either a motorized blower, also called a turbine or compressor, or one or more proportional valves, in place of the motorized blower; in this case, it is supplied with gas, for example with medical air, via a wall outlet supplied by a hospital network that transports gas within a hospital establishment.

In all cases, the medical ventilator 2 delivers the respiratory gas to the patient circuit 3. Its functioning is moreover controlled by one or more electronic control boards or similar, and it is supplied with electricity by electrical power supply means, such as the mains (110/220V) and/or an internal battery.

For example, the medical ventilator 2 can be the Servo-n Néonatal® from Getinge, which is a ventilator with proportional valves and including an HFO function.

As can be seen from FIG. 1, the patient circuit 3 here comprises an inhalation branch 31 and an exhalation branch 32 which are fluidically connected to a joining piece 33, such as a Y-piece or similar, in fluidic communication with a respiratory interface 30 for delivering the gas to the patient P or for collecting the gases exhaled by said patient P. The respiratory interface 30 can be, for example, a face mask, an intubation tube, etc.

The inhalation branch 31 and exhalation branch 32 comprise ducts, channels, hoses, passages, tubes or similar, for example flexible hoses made of polymer which are able and configured to transport the gas flow.

The respiratory gas circulating in the inhalation branch 31 of the patient circuit 3, that is to say going from the mechanical ventilator 2 to the patient P, is inhaled by the patient P, whilst the gases exhaled by said patient P, i.e. gases enriched in $CO_2$, follow the exhalation branch 32 of the patient circuit 3 in the direction of the mechanical ventilator 2 in order to be released to the atmosphere via the mechanical ventilator 2.

Moreover, a flow rate sensor 100 and an NO injection module 110 are arranged in the inhalation branch 31 of the patient circuit 3. The flow rate sensor 100 is preferably arranged in the inhalation branch 31 between the NO injection module 110 and the mechanical ventilator 2, so as to be able to measure the flow rate of gas circulating there, typically a flow of air coming from the mechanical ventilator 2.

The inhalation branch 31 can also comprise a humidifier (not shown) in order to humidify the gas delivered to the patient P. Preferably, the humidifier is placed downstream of the NO injection module 110, that is to say between said NO injection module 110 and the respiratory interface 30 supplying the gas to the patient P.

More precisely, the flow rate sensor 100 is used to measure the gas flow, i.e. a flow rate, delivered by the mechanical ventilator 2 and circulating in the inhalation branch 31, for example a mass-flow sensor or a differential pressure sensor. These flow rate measurements serve to control the quantity of NO provided by the NO delivery device 1, as is explained below.

In the embodiment of FIG. 1, the flow rate sensor 100 is of the type measuring differential pressure, that is to say the flow rate sensor 100 comprises an internal restriction 101 which creates a drop in pressure, thus generating a pressure differential or gradient when a gas flow passes through the internal restriction 101.

More precisely, as can be seen in FIG. 1, the flow rate sensor 100 comprises upstream 120 and downstream 121 chambers which are separated by a wall 122 through which a gas passage extends so as to form the internal restriction 101. An upstream line 103 and a downstream line 102 for pressure measurement are connected fluidically to the flow rate sensor 100 at connection sites situated upstream and downstream of the internal restriction 101, in particular at the upstream 120 and downstream 121 chambers, in order to perform there the pressure measurements on the circulating flow, before and after a pressure drop, typically of the air or a mixture $O_2/N_2$.

The pressure difference created by the internal restriction 101 is determined by a differential pressure sensor 104 connected to the flow rate sensor 100 by way of the upstream line 102 and downstream line 103 which form pressure measurement conduits and supply the differential pressure sensor 104 with the pressure measurements of the circulating flow, before and after a pressure drop. Preferably, the differential pressure sensor 104 is integrated in the casing 10 of the NO delivery device 1 as illustrated in FIG. 1. Moreover, the sensor 104 can either be connected electrically to an operating unit 130, also designated as operating means 130, or can transmit the pressure measurements thereto so that they are processed by computer.

Moreover, a branch line 105 connects to the downstream pressure line 103 in order to carry the information concerning the pressure prevailing in said downstream pressure line 103 to a pressure sensor 106, typically of the relative type. This pressure sensor 106 measures the pressure prevailing in the upstream chamber 120 of the flow rate sensor 100 and can return this value, via an electrical connection, to the operating unit for purposes of compensation, considering that the actual value of the flow rate passing through the flow rate sensor depends principally on the differential pressure measurement 104 but is also affected by the relative pressure 106 prevailing upstream of said flow rate sensor 100.

The operating unit 130, i.e. the operating means 130, comprises a system for processing data, i.e. measurements, typically comprising one or more microprocessors arranged on one or more electronic boards and using one or more algorithms, i.e. one or more computer programs. In other words, the operating unit 130 is configured to process and/or exploit the measurements, that is to say the pressure measurement signals or the pressure values, transmitted by the differential pressure sensor 104 (and pressure sensor 106) cooperating with the flow rate sensor 100.

Of course, the operating unit 130 can also be configured to operate other electromechanical elements integrated in the casing 10 or outer shell of the NO delivery device 1.

In particular, the operating unit 130 has a pre-recorded, i.e. stored, lookup table which permits determination of the flow rate of gas circulating in the inhalation branch 31 and through the flow rate sensor 100, that is to say makes it possible to transform a pressure value transmitted by the differential pressure sensor 104 into a value of the flow rate passing through the flow rate sensor 100 (optionally compensated by the value returned by the pressure sensor 106). This determination of the flow rate of the gaseous flow (i.e. air) passing through the flow rate sensor 100 then makes it possible to calculate the quantity of NO that has to be added to the gas circulating in the inhalation branch 31 before reaching the patient P, so as to be able to deliver the NO in gaseous form to the patient P at the desired concentration corresponding to the dosage fixed by an anaesthetist or similar, typically between 1 and 80 ppmv of NO (i.e. ppm by volume).

In other words, using the pressure measurement returned by the differential pressure sensor 104 and the lookup table, the operating unit 130 is able to determine the flow rate of gas (e.g. air or $N_2/O_2$ with content of $O_2>21\%$ vol.) issuing from the mechanical ventilator 2 and the quantity of NO that has to be added, via the NO injection module 110, in order to obtain the desired concentration of NO, i.e. the dosage defined by the physician, that is to be inhaled by the patient P.

The final gaseous mixture obtained at the NO injection module 110 then principally comprises nitrogen ($N_2$), oxygen ($O_2$) in a content of at least 21% vol., and NO in a content of typically between 1 and 80 ppmv.

More precisely, depending on the gaseous flow rate (i.e. air or $N_2/O_2$) circulating in the inhalation branch 31 and determined with the aid of the flow rate sensor 100, the operating unit 130 determines the quantity of NO, typically a mixture of NO and $N_2$, that has to be added to the gas (e.g. air or $N_2/O2$ with a content of $O_2>21\%$ vol.) circulating in the inhalation branch 31 by the NO injection module 110, in order to obtain the desired final concentration of NO.

The NO delivery device 1 is supplied with gaseous NO, typically as a gaseous mixture $NO/N_2$, coming from an NO source 250 connected fluidically to the NO delivery device 1, in particular to a high-pressure line 116 of said NO delivery device 1, via a supply line 251, such as a flexible conduit or similar. Typically, the NO source 250 is in the form of one or more pressurized cylinders holding a mixture of $NO/N_2$ containing a concentration of NO of generally between 100 and 2000 ppmv, preferably between 200 and 1000 ppmv, for example of the order of 800 ppmv, and stored at a pressure (when completely full) that can be up to 200 to 250 bar abs, or even more.

The $NO/N_2$ mixture is supplied to the injection module 110 by the NO delivery device 1 via an injection line 111, such as a flexible gas conduit.

The injection line 111 is fluidically connected to a high-pressure line 116 of the NO delivery device 1, which high-pressure line 116 has a high-pressure inlet 116a connected fluidically to the NO source in order to be supplied with $NO/N_2$ under pressure, that is to say at a pressure that can be up to 200 bar abs.

The high-pressure line 116, for example a gas passage or conduit, is arranged in the casing 10 of the NO delivery device 1 and comprises a pressure regulator 115 which reduces the pressure of the $NO/N_2$ mixture to a stable value, for example about 4 bar abs or any other suitable pressure. The outlet port of the pressure regulator 115 thus provides a stable pressure in the upstream portion of the injection line 111.

A valve device 113, preferably a solenoid valve, advantageously a proportional solenoid valve, such as the miniature VSO series from Parker for example, is arranged in the device 1 in order to control the flow rate of gaseous NO within the injection line 111. The flow rate of gas circulating in the injection line 111 is measured by a flow rate measurement device 112, also called NO flow rate sensor, arranged on the injection line 111, preferably placed downstream of the solenoid valve 113, as can be seen in FIG. 1.

The pressure regulator 115, the valve device or solenoid valve 113, the NO flow rate sensor 112 and a portion of the injection line 111 are thus arranged in the casing 10 of the NO delivery device 1.

The valve device 113 is configured to be normally in a closed position (i.e. a closed state) in order to prevent all circulation of gas in the injection line 111. To pass to the open position, the valve device 113 has to be controlled by the operating means 130, as is the case during normal functioning of the NO delivery device 1.

Moreover, an NO emergency dosing system 200 is provided which is arranged in the casing 10 of the NO delivery device 1 and which is configured to function in the event of a malfunction of the NO delivery device 1, as is explained below.

The NO emergency dosing system 200 comprises an emergency line 201, also called a bypass line, such as a gas passage, a gas conduit or similar. The emergency line 201 connects fluidically to the injection line 111 at a first connection site 111a situated upstream of the valve device 113, such as a proportional solenoid valve, and here downstream of the pressure regulator 115, and at a second connection site 111b situated downstream of the valve device 113, and preferably downstream of the NO flow rate sensor 112.

In other words, a valve device 113, such as a proportional solenoid valve, and preferably the NO flow rate sensor 112 are situated between the first and second connection sites 111a, 111b of the emergency line 201, that is to say the emergency line 201 bypasses the valve device 113 and preferably the NO flow rate sensor 112, which are situated on the injection line 111. According to another embodiment, the second connection site 111b can be situated downstream of the valve device 113 and upstream of the NO flow rate sensor 112, that is to say between these two elements.

The emergency line 201 comprises, for its part, an emergency solenoid valve 202 and a flow rate control device 210 forming part of the emergency dosing system 200 of the invention. This emergency solenoid valve 202 is configured to be normally in an open position (i.e. an open state) in order to permit circulation of gas in the emergency line 201. During normal functioning of the NO delivery device 1, this emergency solenoid valve 202 is thus controlled by the operating means 130 to be in a closed position (i.e. a closed state) in order to prevent the flow of NO/NO2 from following the emergency line 201.

The flow rate control device 210 forms or comprises a system with a calibrated orifice 204 of the proportional type. It can cover various forms, i.e. arrangements, in particular the one illustrated in FIG. 2 to FIG. 5 and set out in detail below.

The emergency solenoid valve 202 is preferably a solenoid valve of the "all-or-nothing" type having two possible states, namely an open state and a closed state, for example a solenoid valve of the Picosol series from IMI Morgan or of the HDI series from The Lee Company. As has already been mentioned, the emergency solenoid valve 202 is normally open, that is to say, in the absence of an electrical control from the operating unit 130, the emergency solenoid valve 202 is in the open state, i.e. open position, which then allows the gas coming from the NO source to follow the emergency line 201 from the first connection site 111a in the direction of the second connection site 111b. It is the operating means or operating unit 130 that ensure the closure of the emergency solenoid valve 202, that is to say the changing of the latter from the open state to the closed state, i.e. closed position, in order to prevent any circulation of gas in the emergency line 201 when such a flow is not desired, that is to say during normal functioning.

In other words, the operating means 130, i.e. the operating unit, are configured to cooperate with the emergency solenoid valve 202, the flow rate control device 210, the valve device 113 and the flow rate measurement device 112, during normal functioning of the NO delivery device 1.

In the embodiment shown in FIG. 2 to FIG. 5, the flow rate control device 210 forming or comprising a system with a proportional calibrated orifice, that is to say constituting, comprising or forming a calibrated orifice 204 of the proportional type, comprises an actuator means 203 cooperating with a movable element 2042 arranged in a compartment 2041, said movable element 2042 comprising a continuous recess 2043.

However, according to other embodiments, the flow rate control device 210 constituting the calibrated orifice 204 of the proportional type can take another form, for example a device of the type with a needle valve or an assembly comprising a pressure regulator which can be associated with other components and can be set at different output pressures, in order thereby to guarantee different flow rates.

Figure 2:
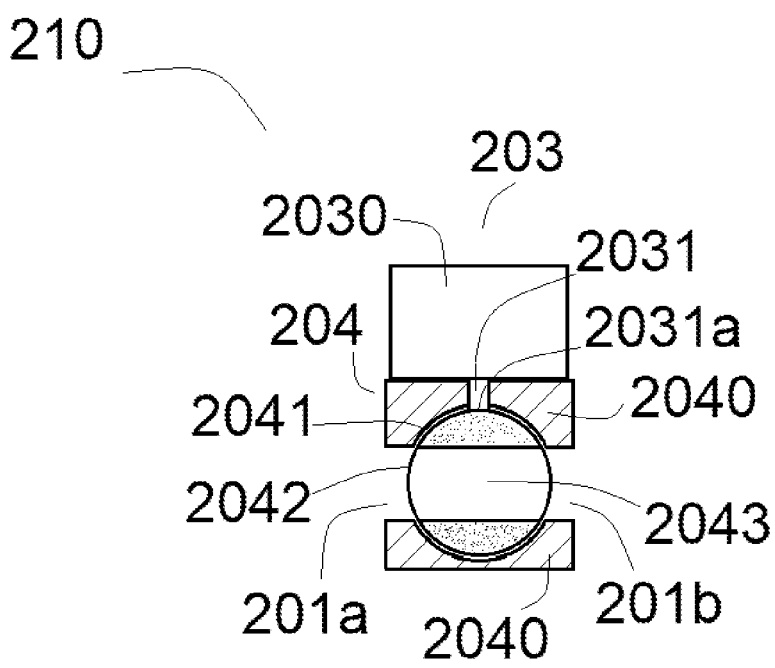
FIG. 2 is a schematic representation of the association between calibrated orifice and actuator in an embodiment of the NO emergency dosing system of FIG. 1.

Thus, FIG. 2 shows a schematic cross section of an embodiment of the flow rate control device 210, i.e. of the calibrated orifice 204, which is here formed by the actuator means 203 and the movable element 2041 associated with the continuous recess 2043, of the NO emergency dosing system with which the NO delivery device 1 is equipped.

The actuator means 203, more simply called the actuator, of FIG. 2 is preferably a stepping motor 2030, for example such as the one sold by Portescap, continued by a shaft 2031 mechanically coupled at 2031a to the movable element 2042.

Moreover, the movable element 2042 is a sphere here. The sphere forming the movable element 2042 can be made of metal, for example of stainless steel, and has a continuous recess 2043, that is to say it is traversed diametrically by an internal drilled hole or passage permitting the passage of the gas. The movable element 2042, i.e. the sphere, is housed in an internal compartment or housing 2041 forming a spherical chamber, which is here of a general spherical shape. The housing 2041 is formed in a part forming a body 2040. The external diameter of the sphere 2042 is substantially equal to the internal diameter of the internal housing 2041.

The part forming a body 2040 can also be made of metal, for example a steel ball or similar. It comprises an inlet port 201a and an outlet port 201b in fluidic communication with the internal housing 2041.

FIG. 2 shows that the continuous recess 2043 of the sphere 2042 is aligned with the inlet port 201a and outlet port 201b of the body 2040, which are in fluidic communication with the emergency line 201, that is to say they are in fluidic continuity, such that the gas is able to flow from the inlet port 201a to the outlet port 201b via the continuous recess 2043 of the sphere 2042.

As indicated, the actuator means 203 is here a stepping motor 2030 driving the shaft 2031 and thus the sphere 2042 in rotation. In response to a command from the operating unit 130, the stepping motor 2030 will adopt a different position and cause a rotation of the shaft 2031, which will then also drive the sphere 2042 in rotation.

Considering that the operating unit 130 is able to vary the control value proportionally, it follows that the shaft 2031 can undergo greater or lesser rotation movements in a proportional manner, for example between 0 and 90°. In other words, the rotation movement performed by the shaft 2031 is thus transmitted to the sphere 2042, which pivots in response, within its housing 2041, as is illustrated in FIG. 3 to FIG. 5, which makes it possible to regulate or adjust the desired flow rate of gas, during the normal functioning of the apparatus 1.

Figure 3:
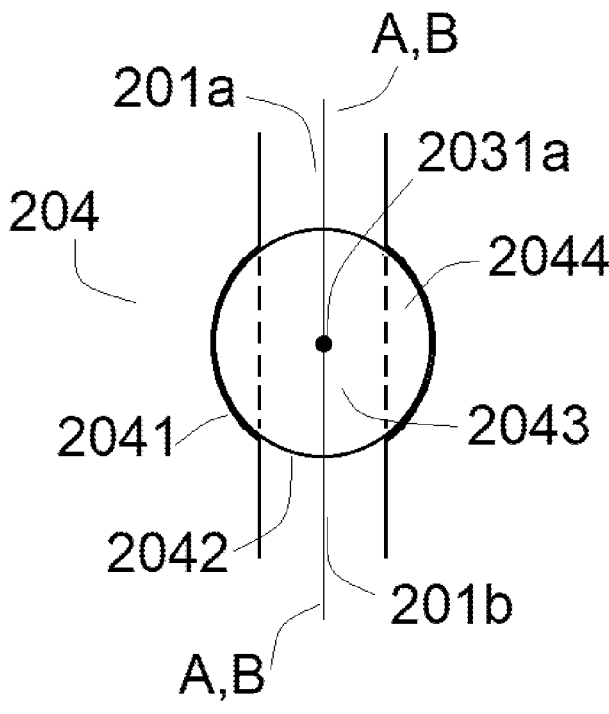
FIG. 3 to FIG. 5 are schematic representations of the functioning of the association between calibrated orifice and actuator of FIG. 2.

Thus, FIG. 3 is a schematic top view of the calibrated orifice of FIG. 2 and shows, as has already been explained, the shaft 2030 which forces the sphere 2042 to present its recess 2043 in continuity with the inlet port 201a and outlet port 201b of the body 2040, so as to create a fluidic connection between said inlet ports 201a, 201b and thus enable the gas to pass through the ports 201a, 201b and the recess 2043. The calibrated orifice 204 is then at its maximum opening, that is to say in a totally open position. In this position, the axis AA of the continuous recess 2043 of the sphere 2042 is (quasi) coaxial with the axis BB passing through the inlet port 201a and outlet port 201b, such that the opening is at its maximum, hence maximum flow in the emergency line 201, including through the continuous recess 2043 of the sphere 2042.

Figure 4:
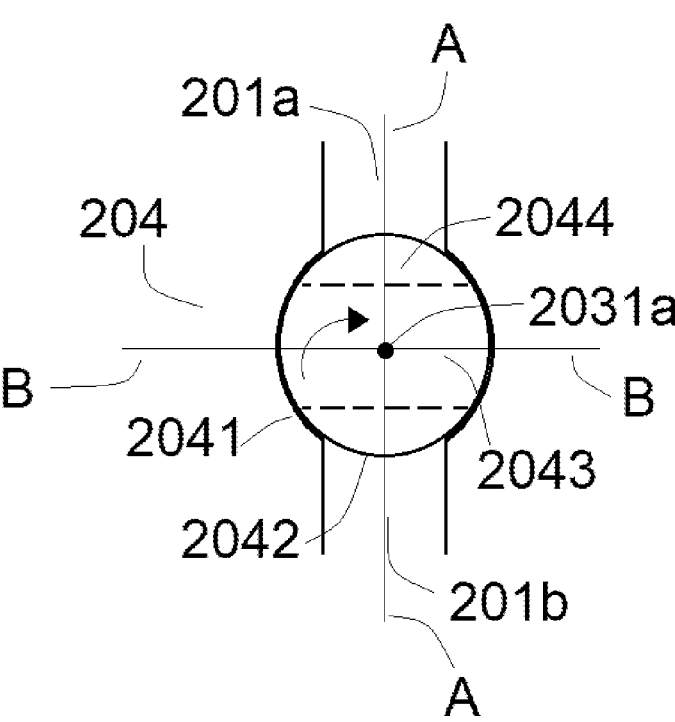
Figure 5:
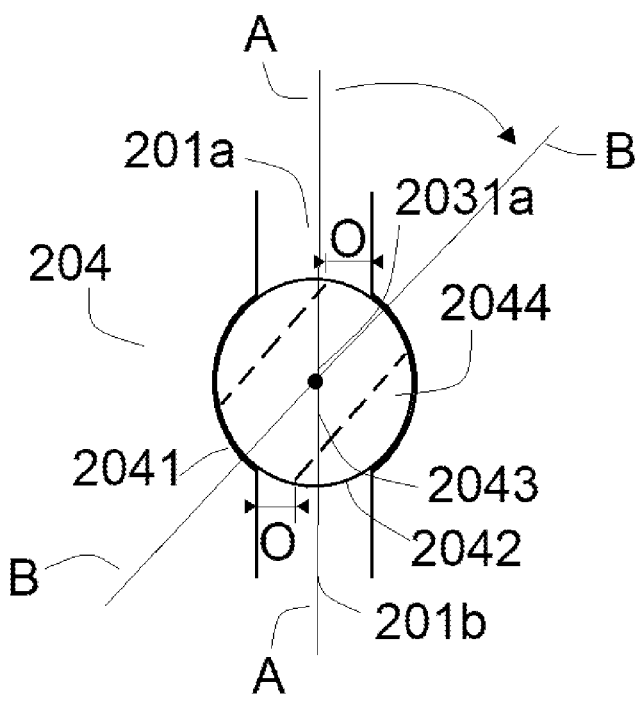

In FIG. 4, the operating unit 130 has controlled the stepping motor 2030 to cause a rotation of the shaft 2031, here of the order of 90°, and therefore also of the sphere 2042, which also undergoes the same rotation of 90°. After rotation, the inlet port 201a and outlet port 201b of the body 2040 of the calibrated orifice 204 no longer face the recess 2043 of the sphere 2042 but instead face a non-recessed, i.e. solid, portion 2044 of the sphere 2042 and are thus completely occluded by the non-recessed part 2044 of the sphere 2042. The fluidic connection is thus interrupted and no gas is able to circulate between the inlet port 201a and outlet port 201b of the body 2040 of the calibrated orifice 204. The calibrated orifice 204 is then totally closed.

In this closed position, the axis AA of the continuous recess 2043 of the sphere 2042 is (quasi) perpendicular to the axis BB passing through the inlet port 201a and outlet port 201b, such that no passage of gas takes place through the continuous recess 2043 and hence through the emergency line 201.

Between FIG. 3 and FIG. 4, the operating unit 130 has imposed on the actuator 203 extreme control values, i.e. between 0° and 90° rotation, making it possible to obtain either complete communication (cf. FIG. 3) or complete isolation (cf. FIG. 4) of the inlet port 201a and outlet port 201b of the body 2040 of the calibrated orifice 204.

However, the operating unit 130 is also configured to be able to issue, in a proportional manner, commands causing a rotation of the shaft 2031 and of the sphere 2042 between these two extreme angular positions, i.e. 0° and 90° rotation, that is to say an angle that is not zero but that is less than 90°.

Thus, FIG. 5 gives the example of an intermediate angular position in which the sphere 2042 has undergone a movement of rotation of the order of 45°. In this case, the inlet port 201a of the body 2040 of the calibrated orifice 204 is partially obstructed, that is to say exposed to non-recessed 2044 and recessed 2043 parts of the sphere 2042. The gas passage cross section of the recessed part 2043 of the sphere 2042 in fluidic communication with the inlet port 201a is then defined by a level (or size) of opening O. This gas passage cross section is always less than the maximum cross section of fluidic connection as shown in FIG. 3. By way of the axial rotation, the same level of opening O appears between the outlet port 201b and the recessed part 2043 of the sphere 2042 of the body 2040 of the calibrated orifice 204.

In what are called the intermediate positions, the axis AA of the continuous recess 2043 of the sphere 2042 and the axis BB passing through the inlet port 210a and outlet port 201b form between them a variable angle, here strictly of between 0 and 90°, such that the passage of gas through the continuous recess 2043, hence in the emergency line 201, is limited/reduced but not zero, nor the maximum, that is to say depending on the desired opening O of the calibrated orifice 204.

Thus, depending on the control imposed on the actuator 203 by the operating unit 130, the level of opening O defined by the intersection of the inlet port 201a, outlet port 201b and the recessed part 2043 of the sphere 2042 varies from a zero value (FIG. 3) to a maximum value (FIG. 4), that is to say it can assume the intermediate values situated between these two extreme values, i.e. between 0 and 90°, which makes it possible to regulate or adjust the flow rate of gas circulating in the emergency line 201.

Indeed, it will be readily appreciated that each level or value of opening O corresponds to an equivalent calibrated orifice whose gas passage diameter depends on the positioning of the sphere 2042 and consequently on the command sent by the operating unit 130, i.e. the operating means, to the actuator 203.

As has already been stated, this assembly thus forms a system with a proportional calibrated orifice, since its diameter or level of opening O depends on the angular position adopted by the sphere 2042 within the body 2040 of the calibrated orifice 204.

However, the pressure prevailing in the upstream portion of the emergency line 201, that is to say upstream of the calibrated orifice 204, is stable and known, since it corresponds to the release pressure of the pressure regulator 115, fixed for example at about 4 bar abs. The flow rate of gas circulating in the downstream portion of the emergency line 201, that is to say downstream of the calibrated orifice 204, therefore depends on the level of opening O.

Thus, the operating unit 130 can have a lookup table linking a given control level to a level of opening and to a flow rate of gas passing through the calibrated orifice 201 in the direction of the injection line 111 and there accessing the second connection site 111b.

For reasons of simplification, it is acknowledged that the pressure level prevailing in the inhalation branch 31 of the patient circuit 3, and therefore in the NO injection module 110 and the injection line 111, is negligible with regard to the release pressure of the pressure regulator 115 and therefore has no impact on the precision of the measurements of the flow rate circulating in the emergency line 201 which are performed by the operating unit 130.

Of course, according to a particular embodiment, supplementary measuring means, such as an additional pressure measurement device arranged to measure pressure downstream of the calibrated orifice 204 of the emergency line 201, can be implemented, i.e. used, for compensation purposes, without changing the subject matter of the present invention.

Finally, it will be noted that the choice of a stepping motor is particularly recommended since, in contrast to the solenoid valves 202, 213 which will adopt a rest position if the power is cut, namely an open position for the all-or-nothing solenoid valve 202 and a closed position for the proportional solenoid valve 113, the position of the stepping motor remains permanent and fixed according to the last command imposed. In other words, the calibrated orifice 204 has a fixed level of opening corresponding to the last control value received by the stepping motor, i.e. the last command originating from the operating means 130.

Of course, the present invention is not limited to an actuator in the form of a stepping motor. In fact, it is possible to use any other actuator that keeps its position if the electrical power supply fails and that can be coupled to a mechanical mechanism so as to define or constitute a system with a calibrated orifice of variable size, for example a linear motor or similar.

Moreover, the NO delivery device 1 is powered electrically by an electrical power supply, for example the mains (110/220V) or an internal battery, in order to permit the correct functioning of the components thereof that require electric current in order to function, in particular the actuator 203, such a stepping electric motor, the operating unit 130, the solenoid valves 202, 13 or others.

In addition, the NO delivery device 1 also comprises storage means, such as a computer memory, for storing data, information or the like, for example one or more lookup tables, the gas flow rate measurements performed by the flow rate measurement device 112, or others.

In the event of the NO delivery device 1 suffering a major failure caused, for example, by its electrical power supply cable being ruptured by vibrations during patient transport for example, or in the case of an electrical power supply failure, one must be able to continue providing treatment to the patient with inhaled NO, this despite the malfunction generating a shut-down of the functioning of the operating means 130, typically on account of an electrical power supply fault.

To this end, the device 1 of the invention is configured such that, in the event of such a fault, the emergency solenoid valve 202 passes to an open position in order to allow gas to circulate in the emergency line 201, while at the same time the valve device 113 passes to a closed position in order to stop any circulation of gas in the injection line 111, which makes it possible to supply the gas, via the emergency line 201 and the flow rate control device 210, at a pre-fixed emergency flow rate of gas.

In fact, during the normal functioning of the device 1 preceding the malfunction, according to the invention said emergency flow rate of gas is determined by the operating means 130 on the basis of one or more gas flow rate measurements supplied by the flow rate measurement device 112 to the operating means 130. The operating means 130 can then pre-regulate the flow rate control device 210 such that the latter can deliver the gas at the pre-fixed emergency flow rate of gas.

In other words, the operating means 130 determine the emergency flow rate of gas, which has to be administered in the event of a breakdown or other malfunction, on the basis of the gas flow rate measurements supplied by the flow rate measurement device 112 during the normal functioning of the device 1 and act on the flow rate control device 210 in order there to regulate this pre-fixed emergency flow rate of gas, for example by acting on the diameter or level of opening O affecting the angular position adopted by the sphere 2042 within the body 2040 of the calibrated orifice 204, as has been explained above.

More precisely, the functioning of the NO emergency dosage system 200 of the NO delivery device 1 of the invention is overall as follows.

As is illustrated in FIG. 1, the NO delivery device 1 cooperates with a mechanical ventilator 2 in order to provide therapeutic aid to the patient P. As has already been explained, the flow rate of gas (i.e. air or $N_2/O_2$) issuing from the mechanical ventilator 2 and circulating in the inhalation branch 31 of the patient circuit 3 is measured permanently by the flow rate sensor 100 and the operating unit 130. This flow rate measurement allows the operating unit 130 to determine, in real time, the flow rate of NO that has to be injected into the injection line 111 and the NO injection module 110 in order to satisfy the desired concentration of NO in the gas supplied to the patient, i.e. typically between 5 and 80 ppmv.

During normal functioning, so as not to introduce an additional flow coming from the emergency line 201 into the injection line 111, the operating unit 130 controls the solenoid valve 202, which is preferably of the all-or-nothing type, in the closed position and, in parallel, will operate the actuator 203, i.e. the stepping motor, in order to pre-regulate the calibrated orifice 204 by defining a given level of opening O.

This is done in the following way by the operating unit 130 on the basis of one or more flow rate measurements from the flow rate measurement device 112, as has already been explained.

The operating unit 130 first of all realises a mean flow rate of NO (i.e. of the mixture $NO/N_2$) that has circulated in the injection line 111 for a given time, for example for 1 minute (or over a longer period of time, but the flow rate must then be converted to l/min), during normal functioning of the device 1. The operating unit 130 then evaluates a fixed mean flow rate of NO (in l/min) making it possible to approach the desired concentration of NO.

When this value has been determined, the operating unit 130 carries out a conversion by way of its stored lookup table in such a way as to control the actuator 203 of the flow rate control device 210 and consequently to define a level of opening of the calibrated orifice 204 in order to enable a flow rate of NO circulating in the emergency line equal to the calculated fixed mean flow rate of NO. It is this calculated mean value of NO that will serve as an emergency flow rate of gas in the event of malfunctioning of the apparatus 1.

It will be noted that this activity has no physical effect, i.e. no flow of gas circulates in the emergency line 201, because the all-or-nothing solenoid valve 202 is closed.

Therefore, in the event of a major failure of the NO delivery device 1 and/or of an interruption in its electricity supply, with the exception of the actuator 203 and of the pressure regulator 115, which have purely pneumatic functioning, all of the electromechanical actuators, in particular the solenoid valves, return to their rest position, and the operating unit 130 and also the various sensors find themselves without an electrical power supply and are therefore unable to communicate and/or to operate/control other components.

As has already been indicated, the proportional solenoid valve 113 recovers its rest position, namely its closed position, preventing any passage of gas, while the solenoid valve 202 at the same time recovers its rest position, namely its open position, enabling passage of the gas coming from the NO source into the emergency line 201 and its circulation as far as the second connection site 111b, then the downstream part of the injection line 111.

The $NO/N_2$ mixture thus circulates in the emergency line 201 at the pre-fixed emergency flow rate which is controlled by the calibrated orifice, namely the last valid value of the fixed mean NO flow rate that has been determined by the operating unit 130 during the normal functioning of the device 1 prior to its malfunctioning.

The emergency flow rate of $NO/N_2$ which rejoins the injection line 111 (at 111b) can then be injected into the inhalation branch 31 of the patient circuit 3 via the NO injection module 110, as has already been explained.

In other words, according to the invention, the flow rate control device 210 is configured to supply the gas, i.e. $NO/N_2$, at a pre-fixed emergency flow rate of gas, where said emergency flow rate of gas is determined by the operating means 130 one the basis of one or more gas flow rate measurements supplied by the flow rate measurement device 112 during a normal functioning of the device 1 prior to the malfunction, for example the last flow rate value that was measured before the malfunction that affects the correct functioning of the device 1.

This flow rate value is pre-regulated within the flow rate control device 210, for example by acting on the angular position adopted by the sphere 2042 within the body 2040 of the calibrated orifice 204 of the flow rate control device 210 in order there to vary the diameter or level of opening O, as has been explained above, by command of said flow rate control device 210 by the operating means 130, said pre-regulation taking place, that is to say being performed or realised, during said normal functioning of the device 1.

Of course, injecting a continuous flow rate of NO into the inhalation branch 31 of the patient circuit 3 does not guarantee the same precision of the inhaled NO concentration as when the NO delivery system 1 operates under normal functioning, that is to say by adjusting the flow rate of NO according to the flow rate passing through the flow rate sensor 100, but the buffer volume generated by the portion of the inhalation branch 31 situated downstream of the NO injection module, which is optionally augmented by the volume of the humidification chamber when the latter is present, makes it possible to smooth the variations in the concentration of NO inhaled by the patient and to come close to the desired target value, that is to say the NO dosage.

In all cases, being able to come close to the desired target value of NO, by virtue of the NO emergency dosing system 200 integrated in the NO delivery device 1 of the invention, considerably improves the safety for the patient by comparison with a fixed NO emergency flow rate (for example of 250 ml/min) usually delivered by the emergency system of the NO delivery devices of the prior art.

Thus, by way of comparison, whilst the emergency NO dosing system 200 integrated in the NO delivery device 1 of the invention is able to guarantee an NO concentration substantially equal to the desired dosage, with an emergency system based on a fixed flow rate of 250 ml/min, as traditionally used in the NO delivery devices of the prior art:

for a mean NO flow rate of 0.05 ml necessary for normally ensuring an NO concentration of 10 ppmv (case of use in neonatology with a ventilator of the HFO type), the concentration resulting with the fixed flow rate of 250 ml/min is 50 ppmv, which corresponds to a five-time multiplication of the desired dosage.

conversely, for a mean NO flow rate of 1 ml/min necessary for ensuring 80 ppmv of NO concentration (case of use in an adult, for example in the case of pulmonary hypertension during heart surgery), the resulting concentration drops to 20 ppmv, which corresponds to a 75% decrease in the desired dosage.

In both cases, the considerable deviations in dosage may bring about situations that are unacceptable and dangerous for the patient, in contrast to the NO emergency dosing system 200 integrated in the NO delivery device 1 of the invention, which makes it possible to comply with the desired dosage.

In other words, the NO emergency dosing system 200 of the invention affords undeniable advantages by increasing patient safety through:

automatically injecting an emergency flow of NO without waiting for the user to recognize the situation and intervene by switching to the emergency pneumatic dosage.

guaranteeing that the NO concentration inhaled by the patient is similar to the concentration desired by the physician, that is to say the desired dosage.

Of course, the switch-over to the NO emergency dosing system 200 of the invention is only temporary, that is to say it lasts only for the time needed to replace the faulty equipment or component that triggered the acoustic and/or visual alarm alerting the medical personnel.

In order to avoid ill-advised activation of the NO emergency dosing system 200, the operating unit 130 is additionally configured to carry out suitable initialization and switch-off sequences. For example, if the NO therapy is deliberately stopped by the user, the operating unit 130 can command the actuator 203 in order to close the calibrated orifice 204. Thus, in the event of deliberate switch-off and thus opening of the solenoid valve 202, the "closed" configuration of the calibrated orifice 204 then prohibits any circulation of NO in the emergency line 201, for the period of time that the NO delivery device 1 is shut down.

The NO delivery device 1 equipped with an NO emergency dosing system 200 according to the invention is particularly suitable for supplying a gaseous mixture comprising 1 to 80 ppmv of NO and at least 21% by volume of oxygen to patients (adults, children, adolescents or neonates) suffering from pulmonary hypertension and/or hypoxia, which can cause pulmonary vasoconstriction or similar, for example caused by pulmonary diseases or disorders such as PPHN (persistent pulmonary hypertension of the newborn) or ARDS (acute respiratory distress syndrome), or those caused by heart surgery with placement of the patient on extracorporeal blood circulation.

The invention claimed is:

1. A nitrogen oxide (NO) delivery device for supplying an NO-containing gas, comprising:

an injection line for conveying the NO-containing gas, a valve device arranged on the injection line for controlling circulation of the NO-containing gas in the injection line, said valve device being configured to be normally in a closed position for preventing any circulation of gas in the injection line, a flow rate measurement device arranged on the injection line for performing one or more measurements of a flow rate of the NO-containing gas circulating in the injection line, an emergency line fluidically connected to the injection line upstream and downstream of the valve device, said emergency line comprising an emergency solenoid valve configured to be normally in an open position for allowing circulation of gas in the emergency line, and a flow rate control device, and operating means configured to cooperate with the emergency solenoid valve, the flow rate control device, the valve device and the flow rate measurement device, wherein, in an event of a malfunction causing shut-down of all cooperation with the operating means:

the emergency solenoid valve is configured to pass to an open position for allowing circulation of gas in the emergency line, the valve device is configured to pass to a closed position in order to stop all circulation of gas in the injection line, and the flow rate control device is configured to supply the NO-containing gas at a pre-fixed emergency flow rate of gas, wherein said emergency flow rate of gas:

is determined by the operating means based on at least one gas flow rate measurement supplied by the flow rate measurement device, during normal functioning of the NO delivery device prior to said malfunction, and is pre-regulated through command of said flow rate control device by the operating means, during said normal functioning of the NO delivery device.

2. The device according to claim 1, wherein the operating means are further configured in order, during the normal functioning of the device, to:

a. command the emergency solenoid valve such that the emergency solenoid valve is in a closed position preventing any circulation of gas in the emergency line, b. command the valve device to enable circulation of gas in the injection line and to permit at least one measurement of gas flow rate to be carried out by the flow rate measurement device, and c. to control the flow rate control device in order to pre-regulate the emergency flow rate of gas based on at least one gas flow rate measurement supplied by the flow rate measurement device.

3. The device according to claim 2, wherein, during the normal functioning of the device, the operating means is further configured to determine the emergency flow rate of gas based on one or more flow rate measurements performed by the flow rate measurement device.

4. The device according to claim 3, wherein the emergency flow rate of gas corresponds to the last flow rate measurement performed by the flow rate measurement device that was performed prior to the malfunction.

5. The device according to claim 2, wherein, during the normal functioning of the NO delivery device, the flow rate measurement device is configured to perform several successive flow rate measurements.

6. An installation for supplying gas to a patient, comprising:

at least one NO source containing a gaseous mixture $NO/N_2$, an NO delivery device according to claim 2, supplied with the gaseous mixture $NO/N_2$ by said at least one NO source, an inhalation branch of a patient circuit supplied with a gaseous mixture $NO/N_2$ by the NO delivery device, and a medical ventilator in fluidic communication with the inhalation branch in order to supply said inhalation branch with a respiratory gas containing at least 21% oxygen.

7. The device according to claim 1, wherein, during the normal functioning of the device, the flow rate measurement device is configured to perform several successive flow rate measurements.

8. The device according to claim 7, further comprising storage means for storing at least some of the successive flow rate measurements performed by the flow rate measurement device.

9. An installation for supplying gas to a patient, comprising:

at least one NO source containing the gaseous mixture $NO/N_2$, an NO delivery device according to claim 7, supplied with the gaseous mixture $NO/N_2$ by said at least one NO source, an inhalation branch of a patient circuit supplied with a gaseous mixture $NO/N_2$ by the NO delivery device, and a medical ventilator in fluidic communication with the inhalation branch in order to supply said inhalation branch with a respiratory gas containing at least 21% oxygen.

10. The device according to claim 1, wherein the emergency solenoid valve is of an all-or-nothing type.

11. The device according to claim 1, wherein the operating means comprises at least one microprocessor.

12. The device according to claim 1, further comprising electrical power supply means for supplying power to at least the operating means.

13. The device according to claim 12, wherein the flow rate control device comprises an actuator means cooperating with a movable element.

14. The device according to claim 13, wherein the actuator means comprises an electric motor powered by the electrical power supply means.

15. The device according to claim 13, wherein the operating means is configured to:

i) determine an opening of a calibrated orifice corresponding to a pre-regulated emergency flow rate, and ii) operate the actuator means to cause a displacement of the movable element to a given position corresponding to said emergency flow rate.

16. The device according to claim 15, wherein the operating means is configured to determine the opening of the calibrated orifice and/or the pre-regulated emergency flow rate based on a stored lookup table.

17. An installation for supplying gas to a patient, comprising:

at least one NO source containing a gaseous mixture NO/nitrogen ($N_2$), the NO delivery device according to claim 1, supplied with the gaseous mixture $NO/N_2$ by said at least one NO source, an inhalation branch of a patient circuit supplied with the gaseous mixture $NO/N_2$ by the NO delivery device, and a medical ventilator in fluidic communication with the inhalation branch in order to supply said inhalation branch with a respiratory gas containing at least 21% oxygen.

18. The installation according to claim 17, wherein the at least one NO source contains the gaseous mixture $NO/N_2$ containing between 100 and 2000 ppmv of NO, the remainder being nitrogen stored at a pressure of between 10 and 250 bar abs.

19. The installation according to claim 17, wherein the respiratory gas is air or an oxygen/nitrogen mixture.

\* \* \* \* \*